United States Patent [19]

Galley et al.

[11] Patent Number: 5,607,681

[45] Date of Patent: Mar. 4, 1997

[54] ANTI-MICROBIAL COMPOSITIONS

[75] Inventors: Edward Galley; Dene C. Godfrey; Walter G. Guthrie; Darren M. Hodgkinson; Helen L. Linnington, all of Nottinghamshire, England

[73] Assignee: The Boots Company PLC, Notts, England

[21] Appl. No.: 916,137

[22] PCT Filed: Jan. 30, 1991

[86] PCT No.: PCT/EP91/00208

§ 371 Date: Jul. 30, 1992

§ 102(e) Date: Jul. 30, 1992

[87] PCT Pub. No.: WO91/11105

PCT Pub. Date: Aug. 8, 1991

[30] Foreign Application Priority Data

Feb. 3, 1990 [GB] United Kingdom .................. 9002422
Nov. 10, 1990 [GB] United Kingdom .................. 9024496

[51] Int. Cl.$^6$ ..................................................... A01N 25/00
[52] U.S. Cl. .............................. 424/405; 424/50; 424/65; 424/400; 424/401
[58] Field of Search ........................................ 424/65, 50

[56] References Cited

U.S. PATENT DOCUMENTS

| | | |
|---|---|---|
| 1,169,998 | 2/1916 | Rhodes . |
| 2,891,868 | 6/1959 | Heggie et al. ............. 99/135 |
| 3,574,824 | 4/1971 | Echeandia et al. . |
| 3,855,142 | 12/1974 | Pader et al. . |
| 4,082,841 | 4/1978 | Pader . |
| 4,150,113 | 4/1979 | Hoogendoorn . |
| 4,178,362 | 12/1979 | Hoogendoorn et al. . |
| 4,282,324 | 8/1981 | Neidleman et al. . |
| 4,320,116 | 3/1982 | Bjorck . |
| 4,370,199 | 1/1983 | Orndorff . |
| 4,473,550 | 9/1984 | Rosenbaum et al. . |
| 4,476,108 | 10/1984 | Kessler et al. . |
| 4,478,693 | 10/1984 | Ray . |
| 4,499,077 | 2/1985 | Stockel et al. . |
| 4,537,764 | 8/1985 | Pellico . |
| 4,564,519 | 1/1986 | Pellico . |
| 4,576,817 | 3/1986 | Montgomery . |
| 4,578,265 | 3/1986 | Pellico . |
| 4,588,586 | 5/1986 | Kessler . |
| 4,617,190 | 10/1986 | Montgomery . |
| 4,726,948 | 2/1988 | Prieels et al. . |
| 4,908,215 | 3/1990 | Perlman . |
| 4,929,451 | 5/1990 | Takenawa et al. . |
| 4,929,466 | 5/1990 | Knutsson . |
| 4,937,072 | 6/1990 | Kessler . |
| 4,978,528 | 12/1990 | Degre . |

FOREIGN PATENT DOCUMENTS

| | | |
|---|---|---|
| 0175801 | 4/1986 | European Pat. Off. . |
| 0252051 | 1/1988 | European Pat. Off. . |
| 0307376 | 3/1989 | European Pat. Off. . |
| 0346909 | 12/1989 | European Pat. Off. . |
| 0366869 | 5/1990 | European Pat. Off. . |
| 0397227 | 11/1990 | European Pat. Off. . |
| 4675M | 9/1964 | France . |
| 2132980 | 11/1972 | France . |
| 52-041224 | 3/1977 | Japan . |
| 57-074076 | 10/1982 | Japan . |
| 62-143672 | 6/1987 | Japan . |
| 6908779 | 12/1969 | Netherlands . |
| 7709302 | 10/1982 | Sweden . |
| 1309282 | 3/1973 | United Kingdom . |
| 1468405 | 3/1977 | United Kingdom . |
| 1546747 | 5/1979 | United Kingdom . |
| 2162063 | 1/1986 | United Kingdom . |
| WO86/04213 | 7/1986 | WIPO . |
| WO87/07838 | 12/1987 | WIPO . |
| WO88/02600 | 4/1988 | WIPO . |

OTHER PUBLICATIONS

Journal of Bacteriology, vol. 99, No. 2, Aug. 1969, R. I. Lehrer: "Antifungal Effects of Peroxidase Systems".

Infection and Immunity, vol. 5, No.1, Jan. 1972, A. A. Jacobs et al: "Mycoplasmicidal Activity of Peroxidase – $H_2O_2$–Halide Systems".

Chemical Abstracts, vol. 89, No.13, 25 Sep. 1978, (Columbus, Ohio, US), J. Delville et al. : "Death and intracellular degradation of mycobacterium leprae after exposure in vitro to enzymic free–radical generators".

Journal of Dental Research, Apr. 1981, E. L. Thomas et al: "Peroxidase Antimicrobial System of Human Saliva and Requirements for Accumulation of Hyopthiocyanite".

The Lactoperoxidase System, Chemistry and Biologocial Significant (1985), Edited by K. M. Pruitt and J. O. Tenovuo, Immunology Series No.27, Published by Marcel Dekker Inc., New York and Basel.

Infection and Immunity, vol. 56, No.12, Dec. 1988, K. Malhotra et al: "Susceptibility of Plasmodium falciparum to a Peroxidase–Mediated Oxygen–Dependent Microbicidal System".

"Sederma" dermatological product – (Manufacturer's information) Mar. 1, 1989.

Elliott and Maynard, "Lactoperoxidase, the Peroxidase in the Salivary Gland" 1968.

Science, vol. 167 (Jan., 1970) pp. 166–167: Peroxidase Mediated Vaucidal.

(List continued on next page.)

Primary Examiner—Shelley A. Dodson
Attorney, Agent, or Firm—Nikaido, Marmelstein, Murray & Oram LLP

[57] ABSTRACT

Anti-microbial compositions are described which contain iodide and thiocyanate anions, an oxidoreductase enzyme, namely glucose oxidase, and its corresponding oxidisable substrate, D-glucose. Such compositions may advantageously further comprise a peroxidase such as lactoperoxidase. The compositions have excellent anti-microbial properties effective against bacteria yeasts and moulds. The compositions may be provided in concentrated substantially non-reacting forms such as dry powders and non-aqueous solutions which may be diluted to provide compositions with broad spectrum anti-microbial activity. Compositions may be used as preservatives or as active agents providing potent anti-microbial activity of use in oral hygiene, deodorant and anti-dandruff products.

52 Claims, No Drawings

OTHER PUBLICATIONS

Iodide–Dependent Catalic Activity of Thyroid Peroxidase and Lactoperoxidase by Ronald P. Magnusson and Alvin Taurog, pp. 475–481; vol. 112, No. 2, 1983; Apr. 29, 1983; Biochemical and Biophysical Research Communications.

Set of "Third Party Observations" mailed Sep. 3, 1993 from the European Patent Office.

The Lactoperoxidase System, Chemistry and Biological Significance (1985), Edited by K. M. Pruitt and J. O. Tenovuo, Immunology Series No. 27, Published by Marcel Dekker Inc., New York and Basel. Chapter 3 pp. 48–50.

Susceptibility of candida albicans to peroxidase–catalyzed oxidation products of thiocyanate, iodide and bromide by P. M. C. Majerus and P. A. P. Courtois, J. Biol. Buccale, vol. 20 pp. 241–245, 1992.

The Catalytic Effect of Peroxidase on the Reaction Between Hydrogen Peroxide and Certain Sulphur Compounds by Sorbo et al, Acta Chem Scan 12 470–476 (1958).

Purification and Iodinating Activity of Hog Thyroid Peroxidase by Coval et al, J. Biol. Chem. vol.242, No.23, pp. 5510–5523 (Dec. 1967).

Studies on the Antibacterial Action of Human Saliva by B. J. Zeldow, J. of Immunology 1963, 90, 12–16 (1963).

Inhibition by Thiocyanate of Lactoperoxidase – Catalyzed Oxidation and Iodination Reactions by J. Tenovuo, Archs. Oral Biol. vol.23, pp. 899–903 (1978).

The Antilactobacillus System of Saliva. Role of Salivary Peroxidase. S. J. Klebanoff et al. Proc. Soc. Exp. Biol. Med. 118, 483 (1965).

The Peroxidase – Thiocyanate – Hydrogen Peroxide Antimicrobial System by S. J. Klebanoff et al. Biochim. Biophys. Acta. 117: 63 (1966).

ANTI-MICROBIAL COMPOSITIONS

The present invention relates to anti-microbial compositions comprising iodide and thiocyanate anions, an oxidoreductase enzyme, namely glucose oxidase, and its corresponding oxidisable substrate, D-glucose. Such compositions may advantageously further comprise a peroxidase such as lactoperoxidase. The compositions have excellent anti-microbial properties effective against bacteria, yeasts and moulds.

It is known that iodide anions and thiocyanate anions may be oxidised in the presence of hydrogen peroxide ($H_2O_2$) to generate oxidation products which are effective bacterial inhibitors. These oxidation reactions may be catalysed by peroxidases such as lactoperoxidase and antibacterial systems containing lactoperoxidase are known. $H_2O_2$ may suitably be provided by a peroxide donor such as sodium percarbonate or may be produced in situ by an oxido-reductase enzyme such as glucose oxidase in the presence of glucose, water and oxygen. Conventional systems based on the oxidation of iodide or thiocyanate anions by $H_2O_2$ are known to provide compositions having short-term bactericidal activity suitable for use as disinfectants e.g. for skin or contact lens sterilisation, milk preservation, or as dental hygiene agents.

EP-A-0307376 (EWOS AG) discloses a short-term microbicidal composition comprising iodide and lactoperoxidase and/or horseradish peroxidase, together with a hydrogen peroxide donor. Optionally, the peroxide donor may be the combination of glucose and glucose peroxidase, but it may also be inter alia magnesium peroxide or carbamide peroxide. When glucose oxidase is included it is present at levels of no more than about 100 U/l. The compositions are only shown to be effective against bacteria and are stated to be active for about 24 hours in open air.

However, the importance of the relative proportions of the components of such systems has not hitherto been fully appreciated and accordingly it has not been possible to develop an oxidation system which provides sustained broad spectrum activity against bacteria, yeasts and moulds.

The applicant has now found that the concentration and relative ratio of such components, in particular of iodide and thiocyanate anions, substantially influences the anti-microbial specificity of such systems. Careful selection of the amounts and relative proportions of each essential component provides anti-microbial compositions having advantageous properties.

Accordingly, the present invention relates to antimicrobial compositions which comprise iodide anions and thiocyanate anions in a weight:weight ratio within the range 0.1:1 to 50:1 and having a combined anion weight concentration of at least 5 mg/kg, D-glucose in a weight concentration of at least 0.2 g/kg, and an effective amount of the oxidoreductase enzyme glucose oxidase. The compositions contain at least 150 U/kg glucose exidase although lower concentrations, for example of 25 U/kg glucose oxidase may be acceptable in compositions which further comprise at least one antioxidant as detailed hereinafter.

In a preferred embodiment of the invention the anti-microbial compositions further comprise a peroxidase such as, for example, lactoperoxidase, myeloperoxidase or horseradish peroxidase. Particularly preferred compositions according to the invention comprise at least 10 U/kg lactoperoxidase.

All units (U) of enzyme activity referred to herein relate to International Units of activity defined as the amount of enzyme required to catalyse the transformation of 1.0 micromole of substrate per minute at 25° C. under optimal conditions. All concentrations referred to herein relate to amounts per kilogram of the total composition.

The term "anti-microbial composition" as used herein embraces compositions having biocidal and/or biostatic activity against various types of micro-organisms, for example gram negative bacteria such as *Escherichia coli* and *Pseudomonas aeruginosa*, gram positive bacteria such as *Staphylococcus aureus* and *Propionibacterium acnes*, moulds such as *Aspergillus niger* and *Penicillium funiculosum*, yeasts such as *Candida albicans, Saccharomvces cerevisiae* and *Pityrosporum ovale*, dermatophytic fungi such as *Trichophyton rubrum*, microalgae such as Chlorella spp. and Spyrogyra spp. and viruses such as Herpes virus and Picornavirus.

Both iodide and thiocyanate anions have been found to be essential components of the compositions according to the invention to ensure that anti-mould and anti-yeast activities are exhibited in addition to the antibacterial activities of the prior art compositions. Iodide and thiocyanate anions are generally included in the compositions according to the invention in the form of salts. Suitable iodide salts include alkali metal salts such as potassium iodide and sodium iodide and mixtures thereof. Suitable thiocyanate salts include, for example, potassium, sodium, ammonium, ferric and cuprous salts of thiocyanate and mixtures thereof. Preferably the weight concentration of iodide anions is at least 5 mg/kg and the weight concentration of thiocyanate anions is at least 2 mg/kg. The weight:weight ratio of iodide:thiocyanate anions is preferably in the range 0.2:1 to 20:1, more preferably 0.5:1 to 15:1, particularly 1:1 to 5:1, and the combined anion weight concentration is preferably at least 10 mg/kg.

The oxidoreductase enzyme, glucose oxidase, catalyses the production of $H_2O_2$ by oxidation of D-glucose in the presence of water and oxygen. It is classified as E.C.1.1.3.4. (IUPAC) and is defined herein in International Units (amount of enzyme required to catalyze the oxidation of 1.0 micromole β-D-glucose per minute at pH 7.0 and 25° C.). Glucose oxidase is available commercially from a number of sources, for example from Sturge-ABM under the trade designation Glucox P200 (2000 U/ml) and Glucox PS (75 U/mg). The applicants have found that both the concentrations and ratios of iodide and thiocyanate anions and the concentration of glucose oxidase used in the compositions according to the invention are critically important for effective control of moulds and yeasts. Compositions according to the invention containing glucose oxidase concentrations in excess of 150 U/kg surprisingly provide excellent protection against bacterial, mould and yeast growth. Comparative compositions containing lower concentrations, for example 75 U/kg of glucose oxidase show adequate antibacterial activity but do not significantly impair mould and yeast growth. In the absence of any further agents which may enhance their anti-microbial activity e.g. antioxidants, such compositions are therefore unacceptable as broad spectrum anti-microbial agents.

The oxidisable substrate for glucose oxidase, namely D-glucose, is generally included in the compositions according to the invention at a concentration of at least 0.5 g/kg, preferably at least 1 g/kg, more particularly at least 2 g/kg. It will be appreciated by those skilled in the art that D-glucose may be provided per se or may be formed in situ within the compositions according to the invention from suitable precursors, for example, as a result of the breakdown of an oligomer or polymer containing D-glucose. Suitable precursors such as sucrose or starch may be used alone or in admixture with D-glucose and may advantageously support more sustained anti-microbial activity than obtained with D-glucose alone. The two other essential substrates for glucose oxidase, namely water and oxygen, are generally present in the environment in which the compositions are to be utilised.

The efficiency of iodide and thiocyanate anion oxidation in the presence of $H_2O_2$ may be enhanced by the addition of small amounts of a peroxidase enzyme such as lactoperoxidase. Thus, compositions according to the present invention preferably further comprise at least 10 U/kg lactoperoxidase, more preferably at least 100 U/kg lactoperoxidase. Lactoperoxidase is classified as E.C.1.17.1.7 (IUPAC) and is defined herein in International Units (amount of enzyme required to catalyse the reduction of 1.0 micromole $H_2O_2$ per minute at pH 7.0 and 25° C.). Lactoperoxidase is available commercially from a number of sources, for example from Swedish Dairies Association (275 U/mg). It may be supplied, for example, in the form of a freeze-dried powder or in an aqueous salt solution e.g. 1.8% NaCl or 12% NaCl. Surprisingly, the compositions according to the invention which further comprise lactoperoxidase prevent microbial spoilage of certain formulation types which have hitherto been difficult to preserve with conventional chemical preservatives.

The essential components of the anti-microbial compositions according to the invention are all derived from naturally occurring systems. The invention therefore provides a "natural" anti-microbial composition which may be used to replace or supplement conventional chemical preservatives used hitherto.

Compositions according to the invention may, if desired, incorporate further agents which may supplement or enhance the anti-microbial activity thereof, for example other enzymes such as lactoferrin or salts such as calcium chloride. Surprisingly, the applicants have found that the anti-microbial activity of the compositions according to the invention is enhanced by the addition of agents having antioxidant activity. Typical antioxidants include, for example, butylated hydroxyanisole, butylated hydroxytoluene, α-tocopherol and esters thereof, ascorbic acid, salts and esters thereof, gallic acid, salts and esters thereof e.g. propyl gallate, quinones such as 2,5-ditertiary butylhydroquinone, propolis, flavenoid-containing materials such as quercetin, sulphur-containing materials such as dilauryl-3,3-thiodipropionate and distearyl-3,3-thiodipropionate,- and mixtures thereof. Compositions according to the invention which comprise at least one antioxidant may, if desired, contain reduced levels of glucose oxidase, for example at least 25 U/kg, preferably at least 75 U/kg glucose oxidase and preferably contain iodide and thiocyanate anions in a weight:weight ratio of 0.1:1 to 20:1. Preferred antioxidants are selected from butylated hydroxyanisole, butylated hydroxytoluene, α-tocopherol and esters thereof and ascorbic acid, salts and esters thereof, preferably in a weight concentration of at least 1 mg/kg, more preferably at least 50 mg/kg. The use of α-tocopherol and esters thereof as "natural" antioxidants is particularly preferred.

One aspect of the invention provides concentrated compositions in substantially non-reacting form which may be stored for prolonged periods prior to use. Concentrated compositions according to the invention will usually maintain physical separation of the glucose oxidase and at least one of its substrates, namely D-glucose, water and oxygen, such that $H_2O_2$ production is substantially prevented during storage. Physical separation may be achieved for example by utilising appropriate formulation techniques, storage conditions or packaging in conventional manner. However, it will be understood that prior to storage concentrated compositions may contain a low level of at least one such substrate sufficient to support an initial reaction but insufficient to sustain activity under the desired storage conditions. The initial reaction may advantageously provide adequate self-preservation of the concentrated compositions according to the invention. Self-preservation is of particular benefit in aqueous concentrates according to the invention which may otherwise require the use of conventional chemical preservatives to avoid microbial spoilage during storage. The substantially non-reacting concentrated compositions according to the invention are intended to be diluted and activated immediately prior to use by bringing the glucose oxidase and substrates thereof into intimate admixture to produce compositions having the desired antimicrobial properties.

The concentrated compositions according to the invention optionally further comprise suitable carriers and/or excipients. Advantageously the compositions may incorporate at least one buffering agent to minimise the fall of pH which may otherwise occur after activation of the concentrated composition. The concentrated compositions may be provided in the form of packs containing one or more discrete units of an appropriate weight or volume for batch or unit dosing.

Concentrated compositions according to the invention may comprise substantially anhydrous mixtures of each of the essential components mentioned hereinbefore, optionally combined with suitable non-aqueous carriers or excipients. Such compositions may be in the form of, for example, powders, compressed tablets, capsules, or anhydrous solutions, pastes or suspensions. The compositions may be stored under anhydrous conditions for example in dessicators, hermetically sealed containers such as sachets, or in evacuated vials, ampoules or pump packs. Activation of such compositions occurs when they are added to an appropriate water-containing diluent.

Concentrated water-containing compositions, optionally combined with suitable carriers or excipients, may be packaged and maintained prior to use under substantially anaerobic conditions. They may be in the form of, for example, solutions, suspensions, pastes or gels. Activation of such compositions occurs when oxygen is admitted into the packaging prior to dilution and use.

Alternatively, compositions may be provided in the form of two or more physically separated phases in which the glucose oxidase is prevented from coming into contact with D-glucose until immediately prior to use. For example, compositions of the present invention may take the form of two or more powders, liquids, pastes or gels which maintain the glucose oxidase and D-glucose in separate phases until the two are physically combined prior to use. Other examples include double layer tablets which are dissolved prior to use and suspensions in which the glucose oxidase or D-glucose is encapsulated until released e.g. by vigorous mixing or by the addition of a component which ruptures the capsules.

Anti-microbial compositions according to the present invention find particular use as preservatives which prevent microbial spoilage of a wide range of products such as, for example, cosmetic, toiletry and pharmaceutical formulations, domestic household and industrial preparations such as, for example, detergents, and foodstuffs such as, for example, milk and milk products and animal feedstuffs.

Preferably the compositions according to the invention are incorporated as preservatives into otherwise conventional formulations suitable, for example, for topical application or pharmaceutical use. The individual components may be added at intervals during formulation of such products or may be added together, preferably in the form of a concentrated composition according to the invention, during or at the end of the formulation process.

A typical preserved composition according to the invention comprises:

(A) 0.5 to 200 mg/kg iodide anions;
(B) 2 to 100 mg/kg thiocyanate anions;
(C) 0.2 to 100 g/kg D-glucose; and
(D) an effective amount of glucose oxidase;

wherein the weight:weight ratio of iodide:thiocyanate anions is 0.1:1 to 50:1 and the combined anion weight concentration is at least 5 mg/kg, in combination with a suitable carrier or excipient. The pH of such compositions is generally between 3 and 9, preferably between 3 and 7, more particularly between pH 4 and 7. Preferably the compositions further comprise (E) 10 to 100000 U/kg lactoperoxidase, more preferably 100 to 25000, most preferably 250 to 10000, particularly 500 to 7000 U/kg lactoperoxidase.

Preserved compositions according to the invention contain 150 to 4000 U/kg, preferably 200 to 3000 U/kg, more preferably 300 to 2500 U/kg glucose oxidase and 1.5 to 50 g/kg, particularly 2.5 to 10 g/kg D-glucose. However, compositions which further comprise at least one antioxidant, for example 1 to 10000 mg/kg, preferably 50 to 5000 mg/kg butylated hydroxytoluene, α-tocopherol or esters thereof or ascorbic acid, esters or salts thereof, may contain lower concentrations of glucose oxidase, for example 25 to 4000 U/kg, preferably 75 to 3000 U/kg glucose oxidase. Advantageously, preserved compositions may further comprise 0.1 to 600 mg/kg of lactoferrin.

In preferred preserved compositions the weight:weight ratio of iodide:thiocyanate anions is 0.2:1 to 20:1, more preferably 0.5:1 to 15:1, particularly 1:1 to 5:1, and the combined anion weight concentration is 5 to 200 mg/kg, preferably 10 to 150 mg/kg. The weight concentration of iodide anions is preferably 1 to 200 mg/kg, more preferably 2 to 150 mg/kg, particularly 5 to 75 mg/kg. The weight concentration of thiocyanate anions is preferably 1 to 100 mg/kg, more preferably 2 to 75 mg/kg, particularly 5 to 50 mg/kg.

The preserved compositions of the invention include cosmetic products such as, for example, skin creams, lotions and foundations; toiletries such as, for example, cleansing lotions, soaps and shampoos; and pharmaceutical preparations such as, for example, ointments, creams, lotions, syrups and suspensions. Compositions may comprise, for example, aqueous or oily solutions or dispersions, oil-in-water or water-in-oil emulsions, pastes, gels or solids. Topically or pharmaceutically acceptable carriers and excipients of use in such preparations will be well known to those skilled in the art.

In addition to their use as preservatives, the anti-microbial compositions of the present invention may provide the active component of a wide variety of products which require potent anti-bacterial, anti-mould and/or anti-yeast activities. Examples of such products include:

a) deodorants e.g. for topical administration in the form of roll-on or stick formulations;
b) antibacterial skin washes e.g. in the form of lotions;
c) anti-acne preparations e.g. in the form of lotions or creams;
d) anti-athletes foot preparations e.g. in the form of lotions;
e) anti-dandruff preparations e.g. in the form of shampoos or lotions;
f) dental preparations e.g. mouth washes suitable for general oral hygiene and in particular having anti-plaque properties, and dentifrices such as toothpastes, toothpowders, chewing gums and lozenges;
g) impregnated materials e.g. wound dressings, sutures and dental floss;
h) pharmaceuticals e.g. wound irrigants and burn treatments, anti-diarrhoeal agents and medicaments suitable for the treatment of infections such as Candida and Tinea infections;
i) ophthalmic preparations e.g. eye washes and solutions for rinsing and/or sterilising contact lenses; and
j) sterilants e.g. for baby bottles and surgical or dental instruments.

The use of the anti-microbial compositions according to the invention in oral hygiene products is particularly advantageous. Broad spectrum antimicrobial activity is an essential requirement of such products, since specificity for a particular group of microorganisms may allow other opportunistic microbes to flourish giving rise to severe infections with one or more specific types of microbe. Furthermore, for organoleptic and safety reasons it would be preferable to use low concentrations of one or more naturally occurring substances if a satisfactory effect could be achieved in this way. In particular, many active ingredients used in conventional oral hygiene products are associated with an unpleasant smell, taste and/or mouthfeel which restricts their use.

A range of oral hygiene preparations may be envisaged which incorporate the anti-microbial compositions of the invention into conventional dental preparations such as mouthwashes, gargles and dentifrices as an anti-plaque agent and/or as a general antiseptic agent, for example in denture cleansing tablets or solutions. The oral hygiene compositions of the present invention may, if desired, contain one or more active ingredients conventionally used in the art. These include, for example, other anti-plaque agents such as bromochlorophene, triclosan, cetylpyridinium chloride and chlorhexidine salts; fluoride ion sources such as sodium fluoride, sodium monofluorophosphate and amine fluorides; anti-tartar agents such as zinc salts, preferably zinc citrate, and water soluble pyrophosphate salts, preferably alkali metal pyrophosphates; and agents which reduce tooth sensitivity including potassium salts such as potassium nitrate and potassium chloride and strontium salts such as strontium chloride and strontium acetate.

The compositions according to the invention may alternatively be provided in concentrated form, for example as a powder, anhydrous solution or effervescent tablet formulation, suitable for dilution in water prior to use as a sterilant of, for example, dental instruments. One preferred use of the anti-microbial compositions of the invention is as toothbrush sanitisers, designed to reduce microbiological contamination of toothbrush heads, for example by overnight soaking every 1 to 14 days of use. Substantial reduction of contamination may be achieved in this way without significant tainting, staining or other adverse effect on the toothbrush.

These so-called "active" uses of the compositions according to the present invention may require higher levels of essential components than those required to provide preservative activity alone. For example, preferred concentrations of components are generally 1 to 50, particularly 2 to 20, more particularly 5 to 15 times higher than the levels mentioned above required to effect adequate broad spectrum anti-microbial activity in compositions in which preservative activity is desirable.

A typical composition for "active" use according to the invention comprises:

A) 10 to 500 mg/kg, preferably 25 to 300 mg/kg iodide anions;

B) 5 to 200 mg/kg, preferably 10 to 150 mg/kg thiocyanate anions;

C) 0.2 to 100 g/kg, preferably 2.5 to 50 g/kg D-glucose;

D) glucose oxidase, preferably 150 to 20000 U/kg, more preferably 500 to 20000 U/kg, particularly 700 to 12000 U/kg glucose oxidase; and, if desired, E) 100 to 100000 U/kg, preferably 500 to 70000 U/kg lactoperoxidase, wherein the weight:weight ratio of iodide:thiocyanate anions is 0.2:1 to 20:1, preferably 0.5:1 to 15:1, more preferably 1:1 to 5:1, and the combined anion weight concentration is at least 25 mg/kg, preferably 25 to 500 mg/kg, in combination with a suitable carrier or excipient.

It will be understood that the concentrated compositions according to the invention as described hereinbefore may be diluted for either active or preservative use. Accordingly, the concentrated compositions may comprise components A:B:C:D:E in the relative ratios (A) 0.0005 to 0.5 g iodide anions:

(B) 0.002 to 0.2 g thiocyanate anions:

(C) 0.2 to 100 g D-glucose:

(D) 25 to 20000 U glucose oxidase:

(E) optionally 10 to 100000 U lactoperoxidase, and wherein the weight:weight ratio of iodide:thiocyanate anions is 0.1:1 to 50:1 and the combined anion weight concentration is at least 25 mg/kg.

The anti-microbial activity of particular compositions according to the present invention has been demonstrated using the following test organisms representative of bacteria, yeasts and moulds:

(i) *Pseudomonas aeruginosa* NCIB 8626

(ii) *Staphylococcus aureus* NCIB 9518

(iii) *Escherichia coli* NCIB 8545

(iv) *Candida albicans* ATCC 10231

(v) *Aspergillus niger* ATCC 16404

(i)–(iv) Each of organisms (i) to (iv) above was inoculated into 100 ml Tryptone Soya Broth (TSB) and incubated at 32° C. for 24 hours on an orbital shaker. 1 ml of the primary culture was transferred to a fresh flask of 100 ml TSB and incubated at 32° C. for 22 hours on an orbital shaker. 0.2 ml of the resulting culture from (i), (ii) or (iii) or 10 ml of the culture from (iv) was pipetted onto a sterile 0.45 μm membrane previously washed with 2×10 ml of Minimal Salts Medium (MSM). The membrane was washed with 2×10 ml MSM, transferred to a sterile vial containing 10 ml MSM+glass beads, and whirlimixed for 1 minute to produce an inoculum of approximately $1.0 \times 10^8$ colony forming units (cfu) per ml.

(v) Organism (v) was subcultured onto a Sabouraud Dextrose agar slope in a 300 ml medical flat and incubated at 25° C. for 7 days. 40 ml MSM+0.05% polyoxyethylene-sorbitan monooleate (Tween 80) was pipetted onto the slope to suspend the *A. niger* spores. The suspension was pipetted onto a 0.45 μm membrane and the membrane washed with 2×10 ml MSM. The membrane was transferred to a sterile vial containing 3 ml MSM+glass beads and whirlimixed for 1 minute to produce an inoculum of approximately $1.0 \times 10^8$ cfu per ml.

All inocula were prepared on the day of use and stored at 4° C.

For each test organism 10 g of the product to be tested was inoculated with 0.1 ml inoculum and mixed thoroughly. The inoculated samples were incubated at 25°–30° C. for the duration of the test. 1 ml samples were removed at appropriate intervals and suitable dilutions plated on Tryptone Soya Agar. Organisms (i) to (iii) were incubated for 3 days at 32° C. and organisms (iv) and (v) were incubated for 5 days at 25° C.

Effective anti-bacterial activity corresponded to a $10^3$ fold reduction of cell count after 48 hours and a total kill after 7 days and at sampling times thereafter. Effective anti-mould and anti-yeast activity corresponded to a $10^2$ fold reduction of cell count after 14 days and no increase of cell count at sampling times thereafter. The expression "adequate preservation against representative bacteria, yeasts and mould" used hereinafter corresponds to effective anti-bacterial, anti-yeast and anti-mould activity shown by a sample of the composition when tested and the results analysed as described above. Samples which failed this test were not considered to be "adequately preserved".

The in vitro biostatic activity of particular compositions according to the present invention has been demonstrated using suitable test organisms such as, for example:

(a) *Staphylococcus aureus* FDA and NCIB 9518

(b) *Pseudomonas aeruginosa* NCIB 11338

(c) *Candida albicans* PH 239

(d) *Trichophyton rubrum* WB 2

(e) *Trichophyton mentagrophytes* PHL 515

(f) *Trichophyton interdigitale* PHL 80

(g) *Propionibacterium acnes* NCTC 737

(h) *Pityrosporum ovale*

(i) *Streptococcus mutans* NCTC 10449

(j) *Streptococcus salivarius* NCIB 8883

Cultures of each organism were freshly prepared using suitable nutrient medium and culture conditions. A suitable inoculum of the test organism (e.g. 0.1 ml of an overnight bacterial TSB culture) was thoroughly mixed into a suitable molten nutrient agar (e.g. 30 ml Tryprone Soya Agar) at 45° C. and poured into petri dishes.

After cooling the seeded agar plates, duplicate wells for each product were cut using a sterile cork borer. The wells were filled with the product to be tested and incubated at an appropriate temperature for a suitable period of time to allow microbial growth to occur (e.g. 37° C. for 18–24 hours for bacteria; 25° C. for 3–5 days for fungi). The inhibition zone surrounding the wells was measured and compared with that of a comparable product e.g. of similar formulation containing an ingredient known to have in vivo biostatic activity, to provide a qualitative assessment of in vitro biostatic activity.

In vitro biostatic activity has been demonstrated against organisms (a) to (j) above. These organisms may be associated with dandruff [particularly organisms (h) and (a-FDA)], plaque [particularly organisms (i) and (j)], athlete's foot [particularly organisms (c), (d), (e) and (f)] and acne [particularly organisms (g) and (a-FDA)]. Activity against organism (a) may also be indicative of deodorant activity.

The anti-plaque activity of particular compositions according to the present invention has also been demonstrated as follows. Thin strips of aluminium were used as an "artificial tooth" surface on which plaque from a small number of donors was grown. Growth was encouraged by the provision of conditions resembling a normal oral environment (saliva, nutrients, pH and temperature) over a two day period with simulations made of the intake of two meals and of a sleeping, low nutrient period. The aluminium strips (and plaque) were exposed for one minute to a solution of a composition according to the invention with distilled water and fresh saliva or a control of distilled water and fresh saliva (six individual strips for each test and control group). Plaque remaining on the strips after rinsing was dispersed by ultrasonic vibration and the optical density of the resulting plaque suspensions at 570 nm (two replicate readings per strip) were used to estimate the percentage reduction in plaque growth compared to the control strips. Statistical significance of the results was estimated using the two-sample t-test.

The invention is illustrated by the following non-limitative Examples 1 to 56. Comparative Examples A to C form no part of the present invention.

EXAMPLE 1

Non-ionic emulsion

|  | Amount/100 g product |
| --- | --- |
| 1) Stearyl polyoxyethylene alcohol (sold under the trade name Brij 72) | 2.0 g |
| 2) Stearyl polyoxyethylene alcohol (sold under the trade name Brij 721) | 1.0 g |
| 3) White soft paraffin | 1.5 g |
| 4) Light liquid paraffin | 4.0 g |
| 5) Cetyl alcohol | 4.0 g |
| 6) Yoghurt powder | 1.0 g |
| 7) Glucose oxidase (sold under the trade designation Glucox P200) | 75 U (37.5 μl at 2 U/μl) 10 ppm |
| 8) D-Glucose (monohydrate) | 0.5 g |
| 9) NaSCN | 1.7 mg (12 ppm SCN⁻) |
| 10) KI | 1.6 mg (12 ppm I⁻) |
| 11) Lactoperoxidase | 550 U (2 mg at 275 U/mg) 20 ppm |
| 12) Water | to 100 g |

Components 1 to 5 were melted together at 65°–70° C. The water, D-glucose and yoghurt powder were heated to 65°–70° C. and then added to the oil phase using a high shear mixer (Silverson) for 10 minutes. The emulsion was force cooled to 30° C. and components 7 and 9–11 (previously dissolved in a small amount of water), were mixed in to give a cream.

This formulation was adequately preserved against representative bacteria, yeasts and mould.

Comparative Examples A

The formulation of Example 1 is difficult to preserve using conventional preservative systems and in the absence of components 7 to 11 failed microbiological testing against representative bacteria, yeasts and mould.

A1. Requirement for iodide and thiocyanate ions

Comparative formulations in which either the iodide (component 10) or the thiocyanate (component 9) was omitted were preserved against representative bacteria but only poorly preserved against representative yeasts and were not preserved against representative mould, indicating that both iodide and thiocyanate anions are required for broad spectrum anti-microbial activity.

A2. Requirement for glucose oxidase and lactoperoxidase

Comparative formulations in which the enzyme components 7 and 11 were omitted failed microbiological testing against representative bacteria, yeasts and mould.

EXAMPLE 2

Non-ionic emulsion

Components 7, 9, 10 and 11 of the formulation described in Example 1 were replaced by different concentrations of each as follows:

|  | Amount/100 g product |
| --- | --- |
| Component 7 (Glucose oxidase) | 37.5 U (18.75 μl at 2 U/μl) 5 ppm |
| Component 9 (NaSCN) | 0.7 mg (5 ppm SCN⁻) |
| Component 10 (KI) | 3.3 mg (25 ppm I⁻) |
| Component 11 (Lactoperoxidase) | 137.5 U (0.5 mg at 275 U/mg) 5 ppm |

This formulation was adequately preserved against representative bacteria, yeasts and mould. Formulations containing higher concentrations of iodide (50 and 100 ppm) were also adequately preserved.

Comparative Examples B

B1. Requirement for five component system

Comparative formulations in which the glucose oxidase (component 7), thiocyanate (component 9) and/or the lactoperoxidase (component 10) of the formulation of Example 2 was omitted, were made up and submitted to microbiological testing for activity against representative bacteria, yeasts and mould.

Good activity against bacteria but only poor activity against yeasts and mould was found when thiocyanate and lactoperoxidase were omitted. Addition of all three components significantly increased the anti-bacterial activity and in addition excellent anti-yeast and anti-mould activity was exhibited.

B2. Effects of reducing glucose oxidase concentration

Component 7 (glucose oxidase) of the formulation described in Example 2 was replaced by glucose oxidase at lower concentrations, namely by 750 or 75 U/kg (2 or 1 ppm). These formulations were adequately preserved against representative bacteria and yeasts but failed against mould.

However, a comparative formulation containing 150 U/kg (2 ppm) glucose oxidase and 200 ppm $CaCl_2$ was adequately preserved against representative bacteria, yeasts and mould.

EXAMPLES 3 to 17

Optimising levels of components in non-ionic emulsion

Components 7, 9, 10 and 11 of the formulation described in Example 1 were replaced by either high or low concentrations of each in a 16-element factorial experiment. Concentrations of each component were as follows:

| Component 7-Glucose oxidase (GO) | 37.5 or 112.5 U/100 g (5 or 15 ppm) |
| --- | --- |
| Component 9-NaSCN | 0.7 or 3.5 mg/100 g (5 or 25 ppm SCN⁻) |
| Component 10-KI | 0.7 or 3.3 mg/100 g (5 or 25 ppm KI) |
| Component 11-Lactoperoxidase (LP) | 137.5 or 687.5 U/100 g (5 or 25 ppm) |

The formulations were submitted to microbiological testing to determine the time taken to achieve zero cell count of representative bacteria, yeasts and mould (kill time). The results are shown in Table 1.

Statistical analysis of the results indicate that for fixed levels of glucose oxidase and lactoperoxidase the most effective concentrations of iodide and thiocyanate are as follows:

| Glucose oxidase (ppm) | Lactoperoxidase (ppm) | Iodide (ppm) | Thiocyanate (ppm) |
|---|---|---|---|
| 15 | 10 | 28.5–25 | 12.5–20 |
| 10 | 15 | 21.5–25 | 5–10 |
| 5 | 5 | 23.5–25 | 6.5–12.5 |

TABLE 1

| | COMPONENT/ppm | | | | END POINT KILL/ | | | |
|---|---|---|---|---|---|---|---|---|
| | 11 | 9 | 7 | 10 | hours (h) or days (d) | | | |
| Example | (LP) | (SCN⁻) | (GO) | (I⁻) | P. aeruginosa | S. aureus | C. albicans | A. niger |
| 3 | 5 | 5 | 5 | 5 | 2.5 h | 14 h | NK | 18 d |
| 4 | 25 | 5 | 5 | 5 | 2.5 h | 14 h | NK | 9 d |
| 5 | 5 | 25 | 5 | 5 | 38 h | 3 d | NK | NK |
| 6 | 25 | 25 | 5 | 5 | 20 h | 48 h | NK | NK |
| 7 | 5 | 5 | 15 | 5 | 2.5 h | 14 h | NK | 14 d |
| 8 | 25 | 5 | 15 | 5 | 2.5 h | 14 h | 21 d | NK |
| 9 | 5 | 25 | 15 | 5 | 38 h | 4 d | 17 d | 28 d |
| 10 | 25 | 25 | 15 | 5 | 29 h | 4 d | NK | NK |
| 2 | 5 | 5 | 5 | 25 | 2.5 h | 2.5 h | 1 d | 2 d |
| 11 | 25 | 5 | 5 | 25 | 2.5 h | 2.5 h | 12 h | 12 h |
| 12 | 5 | 25 | 5 | 25 | 2.5 h | 26 h | 6 d | 2 d |
| 13 | 25 | 25 | 5 | 25 | 2.5 h | 26 h | 10 d | 1 d |
| 14 | 5 | 5 | 15 | 25 | 2.5 h | 5 h | 12 h | 2 d |
| 15 | 25 | 5 | 15 | 25 | 2.5 h | 2.5 h | 12 h | 30 h |
| 16 | 5 | 25 | 15 | 25 | 2.5 h | 26 h | 21 d | 48 h |
| 17 | 25 | 25 | 15 | 25 | 2.5 h | 14 h | 12 h | 12 h |

NK = no kill achieved after 28 days.

EXAMPLE 18

Anionic emulsion

| | Amount/100 g product |
|---|---|
| 1) Acrylic acid copolymer (sold under the trade name Junlon PW110) | 0.35 g |
| 2) Tetrasodium EDTA (sold under the trade name Sequestrene Na4) | 0.1 g |
| 3) Glycerin | 2.0 g |
| 4) Mixture of glycerate/acrylic acid polymer, propylene glycol, methyl paraben and propyl paraben (sold under the trade name Lubrajel) | 2.0 g |
| 5) 1,3-Butylene glycol | 3.0 g |
| 6) Hydrogenated tallow glycerides citrate (sold under the trade name Grindtek CA-P) | 2.0 g |
| 7) Light liquid paraffin | 6.0 g |
| 8) White soft paraffin | 2.0 g |
| 9) Sunflower oil | 2.0 g |
| 10) Cetyl alcohol | 1.0 g |
| 11) Fatty acid cetearate (sold under the trade name Cetiol SN) | 2.5 g |
| 12) KOH | 0.14 g |
| 13) Glucose oxidase (sold under the trade designation Glucox P200) | 37.5 U (18.75 μl at 2 U/μl) 5 ppm |
| 14) D-Glucose (monohydrate) | 0.5 g |
| 15) NaSCN | 0.7 mg (5 ppm SCN⁻) |
| 16) KI | 3.3 mg (25 ppm I⁻) |
| 17) Lactoperoxidase | 137.5 U (0.5 mg at 275 U/mg) 5 ppm |
| 18) Water | to 100 g |

Majority of water (component 18) was heated to 80° C., component 1 was added and the mixture was evenly dispersed using a high shear mixer (Silverson) for 30 minutes. Components 2 to 5 were added and the mixture was heated to 75° C. Components 6 to 11 were mixed together, heated to 75° C. and mixed into the water mixture using the high shear mixer for 5 minutes. Component 12 was added, the mixture homogenised using the high shear mixer for a further 5 minutes and then rapidly cooled to 30° C. Components 13 to 17 (previously dissolved in a small amount of water) were added and the mixture made up to 100 g to give a cream.

This formulation was adequately preserved against representative bacteria, yeasts and mould over a period of one month at room temperature.

Comparative Examples C

Comparative formulations were made up in which one component selected from glucose oxidase, KI, NaSCN and lactoperoxidase was omitted and tested against representative bacteria, yeasts and mould. Results may be summarised as follows:

(i) Omission of glucose oxidase resulted in failure against P. aeruginosa and C. albicans.

(ii) Omission of iodide resulted in failure against yeasts and mould.

(iii) Omission of thiocyanate resulted in failure against mould.

(iv) Omission of lactoperoxidase did not significantly impair preservative activity against bacteria, yeasts or mould.

These results indicate that at least four components, namely glucose oxidase, glucose, iodide and thiocyanate, are essential components required to give broad spectrum anti-microbial activity. Whilst lactoperoxidase is an essential component of the yoghurt-containing non-ionic formulation in Example 1 it does not appear to be essential for broad spectrum preservation of the anionic emulsion formulation of Example 18.

EXAMPLE 19

Anionic emulsion

The formulation of Example 18 was made up with the addition of 50 mg/100 g product (500 ppm) of butylated hydroxytoluene to the oil phase (components 6 to 11).

This formulation was adequately preserved against representative bacteria, yeasts and mould over a period of nine months at room temperature.

EXAMPLE 20

Anionic emulsion

Component 15 of the formulation described in Example 18 was replaced by 1.4 mg (10 ppm $SCN^-$) NaSCN.

This formulation was adequately preserved against representative bacteria, yeasts and mould over a period of six months at room temperature.

In addition to good long-term anti-microbial activity against representative bacteria, yeasts and mould, the formulation of Example 20 was also submitted to short-term microbiological testing against a broad range of bacteria, yeasts and moulds as follows:

BACTERIA - Sample times 2, 4, 24, 72 hours:
- Micrococcus flavus
- Staphylococcus aureus NCIB 9518
- Streptococcus faecalis NCTC 8213
- Pseudomonas aeruginosa NCTC 6750
- Pseudomonas fluorescens NCIB 9046
- Proteus vulgaris NCTC 4635
- Escherichia coli NCTC 5934
- Klebsiella aerogenes NCTC 418
- Enterobacter cloacae 146
- Salmonella typhimurium NCTC 74
- Serratia marcescens YEASTS and MOULDS - Sample times 0, 3, 7 and 14 days:
- Candida albicans ATCC 10231
- Saccharomyces cerevisiae NCYC 87
- Stachybotrys atra IMI 82021
- Myrothecium verrucaria IMI 45541
- Aspergillus niger ATCC 16404
- CladosDorium herbarium 1030
- Penicillium funiculosum IMI 87160
- Trichoderma viride 1096

This formulation showed excellent activity against each of the afore-mentioned microbes when compared to a control formulation in which components 13 to 17 had been omitted.

EXAMPLE 21

Non-ionic emulsion

| | Amount/100 g product |
|---|---|
| 1) A mixture of behenyl dimethyl benzylammonium chloride and propylene glycol (sold under the trade name Incroquat Behenyl BDQP) | 1.0 g |
| 2) Polyoxyethylene stearyl stearate (sold under the trade name Arlatone 985) | 2.0 g |
| 3) Polyoxyethylene stearyl ether (sold under the trade name Brij 76) | 1.6 g |
| 4) Glycerol stearate (sold under the trade name Monostearin NSE Edible Bibby) | 2.0 g |
| 5) Cetyl alcohol | 1.2 g |
| 6) Mineral oil (sold under the trade name Klearol AB&L) | 3.0 g |
| 7) PVP/Hexadecene copolymer (sold under the trade name Unimer U151) | 0.4 g |
| 8) Dimethicone (sold under the trade designation Silicone Fluid F111/20) | 2.0 g |
| 9) Glucose oxidase (sold under the trade designation Glucox P200) | 37.5 U (18.75 µl at 2 U/µl) 5 ppm |
| 10) D-Glucose (monohydrate) | 0.5 g |
| 11) NaSCN | 0.7 mg (5 ppm $SCN^-$) |
| 12) KI | 3.3 mg (25 ppm $I^-$) |
| 13) Lactoperoxidase | 137.5 U (0.5 mg at 275 U/mg) 5 ppm |
| 14) Water | to 100 g |

Components 7 and 14 were mixed and heated to 65°–70° C. Components 1 to 6 and 8 were mixed and heated to 65°–70° C. and then added to the aqueous mixture using a high shear mixer (Silverson) for 10 minutes. The emulsion was rapidly cooled to 30°–35° C. and then components 9 to 13 (previously dissolved in a small amount of water) were added to give a cream.

This formulation was adequately preserved against representative bacteria, yeasts and mould.

EXAMPLE 22

Non-ionic emulsion

Components 11 and 12 of the formulation described in Example 21 were replaced by higher concentrations of each as follows:

| | |
|---|---|
| Component 11 - NaSCN | 4.2 mg (30 ppm $SCN^-$) |
| Component 12 - KI | 6.6 mg (50 ppm $I^-$) |

This formulation was adequately preserved against representative bacteria, yeasts and mould over a period of six months at room temperature.

EXAMPLE 23

Shampoo

| | Amount/100 g product |
|---|---|
| 1) NaCl | 2.5 g |
| 2) Citric acid monohydrate | 50 mg |
| 3) Sodium laureth-2-sulphate (23% solution containing 0.07% formaldehyde) | 25 g |
| 4) Mixture of diethanolamides (sold under the trade name Empilan CDE) | 1 g |
| 5) Butylated hydroxytoluene | 5 mg |
| 6) Glucose oxidase (sold under the trade designation Glucox P200) | 37.5 U (18.75 µl at 2 U/µl) 5 ppm |
| 7) D-Glucose (monohydrate) | 0.5 g |
| 8) NaSCN | 0.7 mg (5 ppm SCN$^-$) |
| 9) KI | 3.3 mg (25 ppm I$^-$) |
| 10) Lactoperoxidase | 137.5 U (0.5 mg at 275 U/mg) 5 ppm |
| 11) Water | to 100 g |

Components 1 and 2 were dissolved in 55% of the water (component 11). Component 3 was stirred into the solution and the mixture heated to 35° C. Component 4 was warmed to 35° C. and component 5 dissolved therein with stirring. The solution of components 4 and 5 was stirred into the aqueous mixture, stirring continued for 10 minutes and then the mixture rapidly cooled to 25°–30° C. Components 6 to 10 were added, the pH adjusted to pH 5-6 if required and the mixture made up to 100 g to give a shampoo.

This formulation was adequately preserved against representative bacteria, yeasts and mould over a period of twelve months at room temperature.

EXAMPLES 24 AND 25

Stick deodorants

| | Amount/100 g product |
|---|---|
| 1) Sodium stearate | 6.0 g |
| 2) Butylene glycol | 70.8 g |
| 3) Oleyl alcohol (sold under the trade name Novol) | 5.0 g |
| 4) Sorbitol | 8.0 g |
| 5) Tetrasodium EDTA (sold under the trade name Sequestrene Na4) | 0.05 g |
| 6) Glucose oxidase (sold under the trade designation Glucox P200) | 375 or 1125 U (188 or 563 µl at 2 U/µl) 50 or 150 ppm |
| 7) D-Glucose (monohydrate) | 5.0 g |
| 8) NaSCN | 7.0 mg (50 ppm SCN$^-$) |
| 9) KI | 33 mg (250 ppm I$^-$) |
| 10) Lactoperoxidase | 1375 U (5 mg at 275 U/mg) 50 ppm |
| 11) Water | to 100 g |

Components 2, 3, 4, 5, 7 and 11 were heated to 75° C., component 1 added and the mixture stirred using a high shear mixer (Silverson) for 10 minutes. Components 6, 8, 9 and 10 (previously dissolved in a small amount of water) were added at approximately 45° C. and the mixture made up to weight with water and stirred well before pouring into deodorant sticks.

Both formulations initially showed good in vitro biostatic activity against two strains of *S.aureus*.

EXAMPLE 26

Sunscreen cream

| | Amount/100 product |
|---|---|
| 1) Cyclomethicone (sold under the trade designation Silicone Fluid 344DC) | 6.0 g |
| 2) A mixture of silicone copolyol and cyclomethicone (sold under the trade designation Silicone Fluid 3225C) | 10.0 g |
| 3) Cetyl dimethicone (sold under the trade name Abil B9801) | 2.0 g |
| 4) Ethoxylated hydrogenated castor oil (sold under the trade name Arlacel 989) | 3.0 g |
| 5) Isopropyl palmitate | 5.0 g |
| 6) Light liquid paraffin | 5.0 g |
| 7) Titanium dioxide coated with aluminium stearate (sold under the trade designation MT100T) | 7.5 g |
| 8) 1,3-Butylene glycol | 3.0 g |
| 9) NaCl | 1.0 g |
| 10) Glucose oxidase (sold under the trade designation Glucox P200) | 37.5 U (18.75 µl at 2 U/µl) 5 ppm |
| 11) D-Glucose (monohydrate) | 0.5 g |
| 12) NaSCN | 0.7 mg (5 ppm SCN$^-$) |
| 13) KI | 3.3 mg (25 ppm I$^-$) |
| 14) Lactoperoxidase | 137.5 U (0.5 mg at 275 U/mg) 5 ppm |
| 15) Water | to 100 g |

Component 7 was added to components 1 to 6 using a high shear mixer (Silverson). Components 8, 9 and 15 were slowly added with constant stirring and then components 10 to 14 were added. The mixture was homogenised using the Silverson for 5 minutes to give a cream.

This formulation was adequately preserved against representative bacteria, yeasts and mould over a period of one month at room temperature.

EXAMPLE 27

Anti-dandruff shampoo

| | Amount/100 g product |
|---|---|
| 1) Sodium laureth-2-sulphate (23% solution containing 0.07% formaldehyde) | 55 g |
| 2) Zinc sulphate | 0.1 g |
| 3) Mixture of diethanolamides (sold under the trade name Empilan CDE) | 5.0 g |
| 4) Stearic acid toilet | 1.0 g |
| 5) Mixture of mono and distearates (sold under the trade name Empilan EGMS) | 3.0 g |
| 6) Glucose oxidase (sold under the trade designation Glucox P200) | 187.5 U (93.75 µl at 2 U/µl) |

|   | Amount/100 g product |
|---|---|
| 7) D-Glucose (monohydrate) | 25 ppm<br>0.5 g |
| 8) NaSCN | 3.5 mg<br>(25 ppm SCN⁻) |
| 9) KI | 16.5 mg<br>(125 ppm I⁻) |
| 10) Lactoperoxidase | 3437.5 U<br>(12.5 mg<br>at 275 U/mg)<br>125 ppm |
| 11) Water | to 100 g |

Components 1, 2 and 11 were heated together to 70° C. Components 3 to 5 were heated together to 70° C. and then added to the aqueous mixture and stirred for 10 minutes. The mixture was cooled rapidly to room temperature and components 6 to 10 added to give a shampoo.

This formulation showed good in vitro biostatic activity, initially and after storage for two months, against *S.aureus* and two strains of *Pityrosporum ovale*.

EXAMPLE 28

Anti-dandruff shampoo

Components 6, 8, 9 and 10 of the formulation described in Example 27 were replaced by different concentrations of each as follows:

| Component 6 (Glucose oxidase) | 750 U<br>(375 μl<br>at 2 U/μl)<br>100 ppm |
|---|---|
| Component 8 (NaSCN) | 16.8 mg<br>(120 ppm SCN⁻) |
| Component 9 (KI) | 15.8 mg<br>(120 ppm I⁻) |
| Component 10 (Lactoperoxidase) | 5500 U<br>(20 mg<br>at 275 U/mg)<br>200 ppm |

This formulation showed good in vitro biostatic activity, initially and after storage for two months, against *S. aureus* (FDA) and two strains of *Pityrosporum ovale*.

EXAMPLE 29

Roll-on deodorant

|   | Amount/100 g product |
|---|---|
| 1) Tetrasodium, EDTA (sold under the trade name Sequestrene Na4) | 0.1 g |
| 2) Mixture of stearates (sold under the trade name Cithrol GMS A/S) | 3.0 g |
| 3) Ethoxylated fatty alcohol (sold under the trade name Cromul EM 0685) | 2.5 g |
| 4) Light liquid paraffin | 3.0 g |
| 5) Glucose oxidase (sold under the trade designation Glucox P200) | 750 U<br>(375 μl<br>at 2 U/μl)<br>100 ppm |
| 6) D-Glucose (monohydrate) | 5.0 g |
| 7) NaSCN | 16.8 mg<br>(120 ppm SCN⁻) |
| 8) KI | 15.8 mg<br>(120 ppm I⁻) |
| 9) Lactoperoxidase | 5500 U<br>(20 mg |

|   | Amount/100 g product |
|---|---|
|   | at 275 U/mg)<br>200 ppm |
| 10) Water | to 100 g |

Components 2, 3 and 4 were mixed and added to a solution of component 1 in water. Components 5 to 9 were added to give a deodorant lotion.

This formulation initially showed good in vitro biostatic activity against two strains of *S.aureus*.

EXAMPLES 30 AND 31

Roll-on deodorants

Components 5, 7, 8 and 9 of the formulation described in Example 29 were replaced by different concentrations of each as follows:

| Component 5 (Glucose oxidase) | 375 or 1125 U<br>(188 or 563 μl at 2 U/μl)<br>50 or 150 ppm |
|---|---|
| Component 7 (NaSCN) | 7 mg<br>(50 ppm SCN⁻) |
| Component 8 (KI) | 33 mg<br>(250 ppm I⁻) |
| Component 9 (Lactoperoxidase) | 1375 U<br>(5 mg at 275 U/mg)<br>50 ppm |

Both formulations initially showed good in vitro biostatic activity against two strains of *S.aureus*.

EXAMPLE 32

Cream for athlete's foot

|   | Amount/100 g product |
|---|---|
| 1) Myristyl ether propionate (sold under the trade name Crodamol PMP) | 16.0 g |
| 2) Capric/caprylic triglyceride (sold under the trade name Miglyol 810) | 15.0 g |
| 3) Cetostearyl alcohol | 2.0 g |
| 4) Blend of fatty alcohols (sold under the trade name Polawax) | 4.0 g |
| 5) Polyethylene glycol | 3.0 g |
| 6) Polyethoxylated cetostearyl alcohol (sold under the trade name Cetomacrogol 1000 BP) | 1.0 g |
| 7) Citric acid monohydrate | 0.18 g |
| 8) Sodium citrate | 0.78 g |
| 9) Glucose oxidase (sold under the trade designation Glucox P200) | 750 U<br>(375 μl at 2 U/μl)<br>100 ppm |
| 10) D-Glucose (monohydrate) | 0.5 g |
| 11) NaSCN | 16.8 mg<br>(120 ppm SCN⁻) |
| 12) KI | 15.8 mg<br>(120 ppm I⁻) |
| 13) Lactoperoxidase | 5500 U<br>(20 mg at 275 U/mg) 200 ppm |
| 14) Water | to 100 g |

Components 7, 8, 10 and 14 were heated to 70° C. Components 1 to 6 were heated to 70° C. and added to components 7, 8, 10 and 14 using a high shear mixer (Silverson) for 10 minutes. The emulsion was rapidly cooled to 30° C. and components 9, 11, 12 and 13 (previously dissolved in a small amount of water) were added and the mixture made up to weight with water.

This formulation showed good in vitro biostatic activity, initially and after storage for four months, against *C.albicans, Trich.rubrum, Trich.mentagrophytes* and *Trich.interdigitale*.

EXAMPLES 33 AND 34

Creams for athlete's foot

Components 9, 11, 12 and 13 of the formulation described in Example 32 were replaced by different. concentrations of each as follows:

| | |
|---|---|
| Component 9 (Glucose oxidase) | 375 or 1125 U |
| | (188 or 563 μl at 2 U/μl) |
| | 50 or 150 ppm |
| Component 11 (NaSCN) | 7 mg |
| | (50 ppm SCN$^-$) |
| Component 12 (KI) | 33 mg |
| | (250 ppm I$^-$) |
| Component 13 (Lactoperoxidase) | 1375 U |
| | (5 mg at 275 U/mg) |
| | 50 ppm |

This formulation showed good in vitro biostatic activity, initially and after storage for four months, against *C.albicans, Trich.rubrum, Trich.mentagrophytes* and *Trich.interdigitale*.

EXAMPLE 35

Glycol paint for athlete's foot or acne

| | Amount/100 g product |
|---|---|
| 1) Propylene glycol | 50 g |
| 2) Glucose oxidase (sold under the trade designation Glucox P200) | 750 U (375 μl at 2 U/μl) 100 ppm |
| 3) D-Glucose (monohydrate) | 0.5 g |
| 4) NaSCN | 16.8 mg (120 ppm SCN$^-$) |
| 5) KI | 15.8 mg (120 ppm I$^-$) |
| 6) Lactoperoxidase | 5500 U (20 mg at 275 U/mg) 200 ppm |
| 7) Water | to 100 g |

Components 1 to 7 were evenly dispersed to give a glycol paint.

This formulation showed good in vitro biostatic activity, initially and after storage for three months, against two strains of *S.aureus* and against *Prop.acnes, C.albicans, Trich.rubrum, Trich. mentagrophytes* and *Trich.interdigitale*.

EXAMPLE 36

Glycol paint for athlete's foot or acne

Components 2, 4, 5 and 6 of the formulation described in Example 35 were replaced by different concentrations of each as follows:

| | |
|---|---|
| Component 2 (Glucose oxidase) | 1125 U |
| | (563 μl at 2 U/μl) |
| | 150 ppm |
| Component 4 (NaSCN) | 7 mg |
| | (50 ppm SCN$^-$) |

-continued

| | |
|---|---|
| Component 5 (KI) | 33 mg |
| | (250 ppm I$^-$) |
| Component 6 (Lactoperoxidase) | 1375 U |
| | (5 mg at 275 U/mg) |
| | 50 ppm |

This formulation showed good in vitro biostatic activity, initially and after storage for three months, against two strains of *S.aureus* and against *Prop.acnes, C. albicans, Trich. rubrum, Trich. mentagrophytes* and *Trich.interdigitale*.

EXAMPLE 37

Sterilant Solution—concentrated tablet

| | Amount/100 g final product |
|---|---|
| 1) Glucose oxidase (sold under the trade designation Glucox PS) | 187.5 U (2.5 mg at 75 U/mg) 25 ppm |
| 2) D-Glucose (monohydrate) | 500 mg |
| 3) NaSCN | 7.0 mg (50 ppm SCN$^-$) |
| 4) KI | 10 mg (75 ppm I$^-$) |
| 5) Lactoperoxidase | 687.5 U (2.5 mg at 275 U/mg) 25 ppm |
| 6) Citric acid | 1072 mg |
| 7) Polyvinylpyrrolidone | 30 mg |
| 8) Sodium bicarbonate (granular) | 1406 mg |

Components 2 and 6 were mixed and granulated with isopropyl alcohol and polyvinylpyrrolidone (Component 7). The granulate was dried and sieved and blended with components 1, 3, 4, 5 and 8. The mixture was compressed in a tabletting machine to give a 3 g concentrated sterilant tablet. One sterilant tablet was dissolved in 100 ml of water immediately prior to use to give a sterilant solution.

EXAMPLE 38

Sterilant Solution—concentrated tablet

| | Amount/100 g final product |
|---|---|
| 1) Glucose oxidase (sold under the trade designation Glucox PS) | 187.5 U (2.5 mg at 75 U/mg) 25 ppm |
| 2) D-Glucose (monohydrate) | 500 mg |
| 3) NaSCN | 7.0 mg (50 ppm SCN$^-$) |
| 4) KI | 10 mg (75 ppm I$^-$) |
| 5) Lactoperoxidase | 687.5 U (2.5 mg at 275 U/mg) 25 ppm |
| 6) Tartaric acid | 1169 mg |
| 7) Sodium bicarbonate (granular) | 1309 mg |
| 8) Polyvinylpyrrolidone | 30 mg |

Components 2 and 6 are mixed and granulated with isopropyl alcohol and polyvinylpyrrolidone (Component 8). The granulate is dried and sieved and blended with components 1, 3, 4, 5 and 7. The mixture is compressed in a tabletting machine to give a 3 g concentrated sterilant tablet. One sterilant tablet is dissolved in 100 ml of water immediately prior to use to give a sterilant solution.

EXAMPLE 39

Sterilant solution—concentrated tablet

|  | Amount/100 g final product |
|---|---|
| 1) Glucose oxidase (sold under the trade designation Glucox PS) | 187.5 U (2.5 mg at 75 U/mg) 25 ppm |
| 2) D-Glucose (monohydrate) | 500 mg |
| 3) NaSCN | 7.0 mg (50 ppm SCN⁻) |
| 4) KI | 10 mg (75 ppm I⁻) |
| 5) Lactoperoxidase | 687.5 U (2.5 mg at 275 U/mg) 25 ppm |
| 6) Adipic acid | 1152 mg |
| 7) Sodium bicarbonate (granular) | 1326 mg |

Components 1 to 7 are sieved and blended and the mixture compressed in a tabletting machine to give a 3 g concentrated sterilant tablet. One sterilant tablet is dissolved in 100 ml of water immediately prior to use to give a sterilant solution.

EXAMPLE 40

Sterilant Solution—concentrated solution

|  | Amount/100 g final product |
|---|---|
| 1) Glucose oxidase (sold under the trade designation Glucox PS) | 187.5 U (2.5 mg at 75 U/mg) 25 ppm |
| 2) D-Glucose (monohydrate) | 500 mg |
| 3) NaSCN | 7.0 mg (50 ppm SCN⁻) |
| 4) KI | 10 mg (75 ppm I⁻) |
| 5) Lactoperoxidase | 687.5 U (2.5 mg at 275 U/mg) 25 ppm |
| 6) Propylene glycol | 9488 mg |

Components 1 to 5 are thoroughly dissolved in component 6 with stirring to give 10 g of concentrated sterilant solution. 10 g of concentrated sterilant solution is dispensed from a measured dose bottle, measured dose pump pack, polymer or glass phial to be diluted with 90 ml of water to give a sterilant solution.

EXAMPLE 41

Sterilant Solution—concentrated powder

|  | Amount 100 g final product |
|---|---|
| 1) Glucose oxidase (sold under the trade designation Glucox PS) | 187.5 U (2.5 mg at 75 U/mg) 25 ppm |
| 2) D-Glucose (monohydrate) | 500 mg |
| 3) NaSCN | 7.0 mg (50 ppm SCN⁻) |
| 4) KI | 10 mg (75 ppm I⁻) |
| 5) Lactoperoxidase | 687.5 U (2.5 mg at 275 U/mg) 25 ppm . |
| 6) Pregel low viscosity starch | 1488 mg |

Components 1 to 6 are sieved and blended and the concentrated sterilant powder is conveniently packaged into a foil-lined sachet, water soluble sachet or water soluble polymer capsule. The concentrated powder is dissolved in 100 ml of water immediately prior to use to give a sterilant solution.

EXAMPLE 42

Sterilant Solution—two pack system e.g. powder and liquid

|  | Amount/100 final product |
|---|---|
| 1) Glucose oxidase (sold under the trade designation Glucox PS) | 187.5 U (2.5 mg at 75 U/mg) 25 ppm |
| 2) NaSCN | 7.0 mg (50 ppm SCN⁻) |
| 3) KI | 10 mg (75 ppm I⁻) |
| 4) Lactoperoxidase | 687.5 U (2.5 mg at 275 U/mg) 25 ppm |
| 5) Sodium chloride | 5000 mg |
| 6) D-glucose (monohydrate) | 500 mg |
| 7) Propylene glycol | 30 g |
| 8) Water | 64.5 ml |

Components 1 to 5 are sieved and blended and the powder is conveniently packaged into a foil-lined sachet, water soluble sachet or water soluble polymer capsule. Component 6 to 8 are stirred together and the powder is mixed into the liquid mixture immediately prior to use to give a sterilant solution.

EXAMPLE 43

Antiplaque Solution

|  | Amount/100 g product |
|---|---|
| 1) Glucose oxidase (sold under the trade designation Glucox P200) | 75 U (37.5 μl at 2 U/μl) 10 ppm |
| 2) D-Glucose (monohydrate) | 500 mg |
| 3) NaSCN | 1.4 mg (10 ppm SCN⁻) |
| 4) KI | 6.7 mg (50 ppm I⁻) |
| 5) Lactoperoxidase | 137.5 U (0.5 mg at 275 U/mg) 5 ppm |
| 6) Propylene glycol | to 100 g |

Components 1 to 5 were freshly dissolved in component 6 immediately prior to use to prepare a solution containing components at a level which could be utilised in a toothpaste preparation.

1 ml of this preparation (approximately equal to a typical aliquot of toothpaste used for cleaning teeth) was mixed with 9 ml of distilled water and 10 ml saliva. A control containing 10 ml saliva and 10 ml of distilled water was used. The antiplaque solution of Example 40 caused a statistically significant ($p<0.05$) reduction (41%) in plaque growth on aluminium strips compared to the control strips.

EXAMPLE 44

Antiplaque Toothpowder

| | | Amount/100 g product |
|---|---|---|
| 1) | Dicalcium phosphate dehydrate | 74.5 g |
| 2) | Precipitated calcium carbonate | 23.0 g |
| 3) | Sodium lauryl sulphate | 1.0 g |
| 4) | Sodium monofluorophosphate | 0.8 g |
| 5) | Glucose oxidase (sold under the trade designation Glucox PS) | 75 U (1 mg at 75 U/mg) 10 ppm |
| 6) | D-Glucose (monohydrate) | 0.5 |
| 7) | NaSCN | 1.4 mg 10 ppm SCN$^-$ |
| 8) | KI | 6.7 mg (50 ppm I$^-$) |
| 9) | Lactoperoxidase | 137.5 U (0.5 mg at 275 U/mg) 5 ppm |
| 10) | Flavour | 1.0 g |
| 11) | Sodium saccharin | 0.2 g |

Components 1 to 11 are sieved and blended to give the antiplaque toothpowder of Example 44.

EXAMPLE 45

Gum Health Toothpowder

| | | Amount/100 g product |
|---|---|---|
| 1) | Dicalcium phosphate dihydrate | 71.1 g |
| 2) | Precipitated calcium carbonate | 20.0 g |
| 3) | Sodium lauryl sulphate | 1.0 g |
| 4) | Tetrasodium pyrophosphate | 2.55 g |
| 5) | Tetrapotassium pyrophosphate | 3.1 g |
| 6) | D-Glucose (monohydrate) | 0.5 g |
| 7) | Lactoperoxidase | 137.5 U (0.5 mg at 275 U/mg) 5 ppm |
| 8) | NaSCN | 1.4 mg (10 ppm SCN$^-$) |
| 9) | KI | 6.7 mg (50 ppm I$^-$) |
| 10) | Glucose oxidase (sold under the trade designation Glucox PS) | 75 U (1 mg at 75 U/mg) 10 ppm |
| 11) | Flavour | 1.0 g |
| 12) | Sodium saccharin | 0.2 g |

Components 1 to 12 are sieved and blended to give the gum health toothpowder of Example 45.

EXAMPLE 46

Gum Health Mouthwash—concentrated tablet formulation

| | | Amount/100 g final product |
|---|---|---|
| 1) | Citric acid | 718 mg |
| 2) | Sodium bicarbonate granular | 943 mg |
| 3) | D-Glucose (monohydrate) | 500 mg |
| 4) | Lactoperoxidase | 137.5 U (0.5 mg at 275 U/mg) 5 ppm |
| 5) | NaSCN | 1.4 mg (10 ppm SCN$^-$) |
| 6) | KI | 6.7 mg (50 ppm I$^-$) |
| 7) | Glucose oxidase (sold under the trade designation Glucox PS) | 75 U (1 mg at 75 U/mg) 10 ppm |
| 8) | Zinc citrate | 100 mg |
| 9) | Flavour | 200 mg |
| 10) | Sodium saccharin | 30 mg |

Components 1 to 10 are sieved and blended and the mixture compressed in a tabletting machine to give 0.5 g concentrated mouthwash tablets. One tablet is dissolved in 20 ml of water immediately prior to use to give the mouthwash of Example 46.

EXAMPLE 47

Antiplaque chewable tablet

| | | Amount/100 g product |
|---|---|---|
| 1) | Citric acid | 0.5 g |
| 2) | Magnesium stearate | 1 g |
| 3) | D-Glucose (monohydrate) | 500 mg |
| 4) | Lactoperoxidase | 137.5 U (0.5 mg at 275 U/mg) 5 ppm |
| 5) | NaSCN | 1.4 mg (10 ppm SCN$^-$) |
| 6) | KI | 6.7 mg (50 ppm I$^-$) |
| 7) | Glucose oxidase (sold under the trade designation Glucox PS) | 75 U (1 mg at 75 U/mg) 10 ppm |
| 8) | Flavour | 2 g |
| 9) | Colour | 0.2 g |
| 10) | Sorbitol (directly compressable granular sorbitol sold under the trade name Sorbit Instant) | to 100 g |

Components 1 to 10 are sieved and blended and the mixture compressed in a tabletting machine to give 1 g chewable tablets of Example 47.

EXAMPLE 48

Concentrated solution

| | | Amount/100 g product |
|---|---|---|
| 1) | Glucose oxidase (sold under the trade designation Glucox P200) | 3750 U (1.875 ml at 2000 U/ml) 500 ppm |
| 2) | D-Glucose (anhydrous) | 40 g |
| 3) | NaSCN | 420 mg (3000 ppm SCN$^-$) |
| 4) | KI | 660 mg (5000 ppm I$^-$) |
| 5) | Lactoperoxidase | 13750 U (50 mg at 275 U/mg) 500 ppm |
| 6) | Water | to 100 g |

Components 1 to 6 are stirred together to give 100 g of concentrated solution. 10 g of concentrated solution is dispensed, for example from a measured dose bottle, measured dose pump pack, polymer or glass phial, and thoroughly mixed with each 1 kg of formulation to be preserved.

EXAMPLE 49

Two pack concentrate

|   | Amount/100 g product |
|---|---|
| 1) Glucose oxidase (sold under the trade designation Glucox P200) | 37500 U (18.75 ml at 2000 U/ml) 5000 ppm |
| 2) D-Glucose (anhydrous) | 25 mg |
| 3) NaSCN | 4.2 g (30000 ppm SCN⁻) |
| 4) KI | 6.6 g (50000 ppm I⁻) |
| 5) Lactoperoxidase | 137500 U (500 mg at 275 U/mg) 5000 ppm |
| 6) Water | to 100 g |
| 7) D-Glucose (anhydrous) | 400 g |

Components 1 to 6 are stirred together to give 100 g of concentrated solution. Component 7 is conveniently packaged into a water impermeable sachet. The concentrated solution and the contents of the sachet are thoroughly mixed with each 500 kg of formulation to be preserved.

EXAMPLE 50

Two pack concentrate

|   | Amount/100 g product |
|---|---|
| 1) Glucose oxidase (sold under the trade designation Glucox P200) | 3750 U (1.875 ml at 2000 U/ml) 500 ppm |
| 2) D-Glucose (anhydrous) | 25 mg |
| 3) NaSCN | 0.42 g (3000 ppm SCN⁻) |
| 4) KI | 0.66 g (5000 ppm I⁻) |
| 5) Lactoperoxidase | 13750 U (50 mg at 275 U/mg) 500 ppm |
| 6) α-Tocopheryl acetate | 25 g |
| 7) Water | to 100 g |
| 8) D-Glucose (anhydrous) | 40 g |

Components 1 to 7 are stirred together to give 100 g of concentrated solution. Component 8 is conveniently packaged into a water impermeable sachet. The concentrated solution and the contents of the sachet are thoroughly mixed with each 50 kg of formulation to be preserved.

EXAMPLE 51

Syrup for pharmaceutical use

|   | Amount/100 g product |
|---|---|
| 1) Glucose oxidase (sold under the trade designation Glucox P200) | 56 U (28 µl at 2 U/µl) 7.5 ppm |
| 2) D-Glucose (anhydrous) | 0.5 mg |
| 3) NaSCN | 4.2 mg (30 ppm SCN⁻) |
| 4) KI | 6.6 mg (50 ppm I⁻) |
| 5) Lactoperoxidase | 137.5 U (0.5 mg at 275 U/mg) 5 ppm |
| 6) Sucrose | 66.7 g |
| 7) Purified water BP | to 100 g |

Majority of water (component 7) was heated to 60° C., component 6 was added and the mixture stirred until dissolved. Components 1 to 5 were added to the cooled mixture which was stirred and made up to 100 g to give a syrup suitable for pharmaceutical use.

This formulation was adequately preserved against representative bacteria, yeasts and mould.

EXAMPLE 52

Eye drops

|   | Amount/100 g product |
|---|---|
| 1) Glucose oxidase (sold under the trade designation Glucox P200) | 56 U (28 µl at 2 U/µl) 7.5 ppm |
| 2) D-Glucose (anhydrous) | 0.5 g |
| 3) NaSCN | 4.2 mg (30 ppm SCN⁻) |
| 4) KI | 6.6 mg (50 ppm I⁻) |
| 5) Lactoperoxidase | 137.5 U (0.5 mg at 275 U/mg) 5 ppm |
| 6) Hypromellose 4500 BP | 0.3 g |
| 7) Borax BP | 0.19 g |
| 8) Boric acid BP | 0.19 g |
| 9) Potassium chloride BP | 0.37 g |
| 10) Sodium chloride BP | 0.45 g |
| 11) Purified water BP | to 100 g |

50 ml water (component 11) was heated to 80° C., component 6 was added and the mixture stirred until evenly dispersed. The solution was cooled to below 40° C., remaining components 1 to 5 and 7 to 10 stirred in and the solution made up to 100 g with water.

This formulation was adequately preserved against representative bacteria, yeasts and mould.

EXAMPLE 53

Buffered cream for pharmaceutical use

|   | Amount/100 g product |
|---|---|
| 1) Glucose oxidase (sold under the trade designation Glucox P200) | 56 U (28 µl at 2 U/µl) 7.5 ppm |
| 2) D-Glucose (anhydrous) | 0.5 g |
| 3) NaSCN | 4.2 mg (30 ppm SCN⁻) |
| 4) KI | 6.6 mg (50 ppm I⁻) |
| 5) Lactoperoxidase | 137.5 U (0.5 mg at 275 U/mg) 5 ppm |
| 6) Emulsifying wax BP | 9 g |
| 7) Liquid paraffin BP | 6 g |
| 8) White soft paraffin BP | 15 g |
| 9) Sodium phosphate (anhydrous) | 1 g |
| 10) Citric acid monohydrate BP | 0.5 g |
| 11) Purified water BP | to 100 g |

Components 6 to 8 were melted together. Components 9 and 10 dissolved in majority of water were stirred in and the mixture was homogenised using a high shear mixer. Components 1 to 5 were stirred in and the mixture made up to 100 g to give a buffered cream suitable for pharmaceutical use.

This formulation was adequately preserved against representative bacteria, yeasts and mould.

EXAMPLE 54

Aqueous cream for pharmaceutical use

|   | | Amount/100 g product |
|---|---|---|
| 1) | Glucose oxidase (sold under the trade designation Glucox P200) | 56 U (28 µl at 2 U/µl) 7.5 ppm |
| 2) | D-Glucose (anhydrous) | 0.5 g |
| 3) | NaSCN | 4.2 mg (30 ppm SCN⁻) |
| 4) | KI | 6.6 mg (50 ppm I⁻) |
| 5) | Lactoperoxidase | 137.5 U (0.5 mg at 275 U/mg) 5 ppm |
| 6) | Emulsifying wax BP | 9 g |
| 7) | Liquid paraffin BP | 6 g |
| 8) | White soft paraffin BP | 15 g |
| 9) | Purified water BP | to 100 g |

Components 6 to 8 were melted together. Majority of water was stirred in and the mixture was homogenised using a high shear mixer. Components 1 to 5 were stirred in and the mixture made up to 100 g to give an aqueous cream suitable for pharmaceutical use.

This formulation was adequately preserved against representative bacteria, yeasts and mould.

EXAMPLE 55

Antacid suspension

|   | | Amount/100 g product |
|---|---|---|
| 1) | Glucose oxidase (sold under the trade designation Glucox P200) | 56 U (28 µl at 2 U/µl) 7.5 ppm |
| 2) | D-Glucose (anhydrous) | 0.5 g |
| 3) | NaSCN | 4.2 mg (30 ppm SCN⁻) |
| 4) | KI | 6.6 mg (50 ppm I⁻) |
| 5) | Lactoperoxidase | 137.5 U (0.5 mg at 275 U/mg) 5 ppm |
| 6) | Dimethicone | 2.7 g |
| 7) | Magnesium hydroxide pumpable 30 USP | 7.0 g |
| 8) | Aluminium hydroxide suspension (sold under the trade name Liquigel D4 by Reheis Ltd) | 40.0 g |
| 9) | Sodium saccharin BP | 3 mg |
| 10) | Non-crystalline sorbitol solution BP | 2.0 g |
| 11) | Flavouring | 0.5 g |
| 12) | Purified water BP | to 100 g |

Component 6 was mixed into majority of water using a high shear mixer. Remaining components were stirred in and the mixture made up to 100 g to give an antacid suspension.

This formulation was adequately preserved against representative bacteria, yeasts and mould.

EXAMPLE 56

Eye lotion

|   | | Amount/100 g product |
|---|---|---|
| 1) | Glucose oxidase (sold under the trade designation Glucox P200) | 56 U (28 µl at 2 U/µl) 7.5 ppm |
| 2) | D-Glucose (anhydrous) | 0.5 g |
| 3) | NaSCN | 4.2 mg (30 ppm SCN⁻) |
| 4) | KI | 6.6 mg (50 ppm I⁻) |
| 5) | Lactoperoxidase | 137.5 U (0.5 mg at 275 U/mg) 5 ppm |
| 6) | Hamamelis water BPC | 13.0 g |
| 7) | Sodium citrate BP | 1.0 g |
| 8) | Citric acid monhydrate BP | 0.01 g |
| 9) | Purified water BP | to 100 g |

Components 1 to 9 were stirred together to give an eye lotion.

This formulation was adequately preserved against representative bacteria, yeasts and mould.

We claim:

1. A composition which comprises iodide anions and thiocyanate anions in a weight:weight ratio within the range 0.1:1 to 50:1 and having a combined anion weight concentration of at least 5 mg/kg, D-glucose in a weight concentration of at least 0.2 g/kg, and either:

a) at least 150 U/kg glucose oxidase; or b) at least 25 U/kg glucose oxidase and at least one antioxidant.

2. A composition as claimed in claim 1 which further comprise an effective amount of one or more peroxidase.

3. A composition as claimed in claim 2 which comprises at least 10 U/kg lactoperoxidase.

4. A composition as claimed in claim 1 in which the weight concentration of iodide anions is at least 5 mg/kg and the weight concentration of thiocyanate anions is at least 2 mg/kg.

5. A composition as claimed in claim 1 in which the weight:weight ratio of iodide:thiocyanate anions is 0.2:1 to 20:1.

6. A composition as claimed in claim 1 which comprise at least one antioxidant.

7. A composition as claimed in claim 6 in which the antioxidant is selected from butylated hydroxyanisole, butylated hydroxytoluene, α-tocopherol and esters thereof and ascorbic acid, salts and esters thereof.

8. A composition which comprises:

(A) 0.5 to 200 mg/kg iodide anions;

(B) 2 to 100 mg/kg thiocyanate anions;

(C) 0.2 to 100 g/kg D-glucose; and (D) either:

a) 150 to 4000 U/kg glucose oxidase; or b) 25 to 4000 U/kg glucose oxidase and at least one antioxidant;

wherein the weight:weight ratio of iodide:thiocyanate anions is 0.1:1 to 50:1 and the combined anion weight concentration is at least 5 mg/kg, in combination with a carrier or excipient.

9. A composition as claimed in claim 8 which further comprises:

(E) 10 to 100000 U/kg lactoperoxidase.

10. A composition as claimed in claim 8 in which the weight:weight ratio of iodide:thiocyanate anions is 0.2:1 to 20:1.

11. A composition as claimed in claim 10 in which the combined anion weight concentration is 5 to 200 mg/kg.

12. Composition which comprises:
   (A) 10 to 500 mg/kg iodide anions;
   (B) 5 to 200 mg/kg thiocyanate anions;
   (C) 0.2 to 100 g/kg D-glucose; and
   (D) 150 to 20000 U/kg glucose oxidase;
wherein the weight:weight ratio of iodide:thiocyanate anions is 0.2:1 to 20:1 and the combined anion weight concentration is at least 25 mg/kg, in combination with a carrier or excipient.

13. A composition as claimed in claim 12 which further comprises 100 to 100000 U/kg lactoperoxidase.

14. A composition as claimed in claim 12 which is a deodorant, anti-acne, anti-athletes foot, anti-dandruff or oral hygiene product.

15. A composition as claimed in claim 1 in concentrated and substantially non-reacting form.

16. A concentrated composition for dilution to provide a composition as claimed in claim 1 which comprise components A:B:C:D:E in the relative ratios
   (A) 0.0005 to 0.5 g iodide anions:
   (B) 0.002 to 0.2 g thiocyanate anions:
   (C) 0.2 to 100 g D-glucose:
   (D) 25 to 20000 U glucose oxidase:
   (E) optionally 10 to 100000 U lactoperoxidase, and
wherein the weight:weight ratio of iodide:thiocyanate anions is 0.1:1 to 50:1 and the combined anion weight concentration is at least 25 mg/kg, in substantially non-reacting form.

17. A concentrated composition as claimed in claim 15 in unit dosage form.

18. A process of preserving a material comprising adding to said material an anti-microbial composition as claimed in claim 1.

19. A method of providing an anti-microbial effect to a material, comprising adding to said material a composition as claimed in claim 15.

20. A process of preserving a material, comprising adding to said material a concentrated composition as claimed in claim 15.

21. A composition as recited in claim 15, wherein said composition is in a form in which substantially all of said D-glucose is physically separated from said glucose oxidase in order to provide said substantially non-reacting form.

22. A composition as recited in claim 21, wherein a low level of said D-glucose is in contact with said glucose oxidase to provide self-preservation.

23. A composition as recited in claim 21 wherein said composition further comprises water and oxygen.

24. A composition as recited in claim 21, wherein said composition further comprises lactoperoxidase.

25. A composition as recited in claim 15, wherein said composition further comprises water and is in a form in which substantially all of said water is physically separated from said glucose oxidase in order to provide said substantially non-reacting form.

26. A composition as recited in claim 25, wherein a low level of said water is in contact with said glucose oxidase to provide self-preservation.

27. A composition as recited in claim 25, wherein said composition further comprises oxygen.

28. A composition as recited in claim 25, wherein said composition further comprises lactoperoxidase.

29. A composition as recited in claim 15, wherein said composition further comprises oxygen and is in a form in which substantially all of said oxygen is physically separated from said glucose oxidase in order to provide said substantially non-reacting form.

30. A composition as recited in claim 29, wherein a low level of said oxygen is in contact with said glucose oxidase to provide self-preservation.

31. A composition as recited in claim 29, wherein said composition further comprises water.

32. A composition as recited in claim 29, wherein said composition further comprises lactoperoxidase.

33. A composition as recited in claim 15, wherein said composition is substantially anhydrous in order to provide said substantially non-reacting form.

34. A composition as recited in claim 33, wherein said composition further comprises oxygen.

35. A composition as recited in claim 33, wherein said composition further comprises lactoperoxidase.

36. A composition as recited in claim 15, wherein said composition is substantially anaerobic in order to provide said substantially non-reacting form.

37. A composition as recited in claim 36, wherein said composition further comprises water.

38. A composition as recited in claim 36, wherein said composition further comprises lactoperoxidase.

39. A composition as recited in claim 15, wherein said composition is in the form of at least two physically separated phases in which said glucose oxidase is prevented from coming into contact with said D-glucose in order to provide said substantially non-reacting form.

40. A composition as recited in claim 39, wherein said composition further comprises water.

41. A composition as recited in claim 39, wherein said composition further comprises oxygen.

42. A composition as recited in claim 39, wherein said composition further comprises lactoperoxidase.

43. A kit comprising:
   at least a first phase and a second phase which, when combined, provide a composition which comprises:
      iodide anions and thiocyanate anions in a weight:weight ratio within the range 0.1:1 to 50:1 and having a combined anion weight concentration of at least 5 mg/kg, D-glucose in a weight concentration of at least 0.2 g/kg, and at least 150 U/kg glucose oxidase,
   said first and second phases being physically separated, said first phase comprising said glucose oxidase and said second phase comprising substantially all of said D-glucose.

44. A composition as recited in claim 43, wherein a low level of said D-glucose is in contact with said glucose oxidase to provide self-preservation.

45. A kit as recited in claim 43, wherein said composition further comprises water.

46. A kit as recited in claim 43, wherein said composition further comprises oxygen.

47. A kit as recited in claim 43, wherein said composition further comprises lactoperoxidase.

48. A kit comprising:
   at least a first phase and a second phase which, when combined, provide a composition which comprises:
      iodide anions and thiocyanate anions in a weight:weight ratio within the range 0.1:1 to 50:1 and having a combined anion weight concentration of at least 5 mg/kg, D-glucose in a weight concentration of at least 0.2 g/kg, at least 25 U/kg glucose oxidase, and at least one antioxidant,
   said first and second phases being physically separated, said first phase comprising said glucose oxidase and said second phase comprising substantially all of said D-glucose.

49. A composition as recited in claim 48, wherein a low level of said D-glucose is in contact with said glucose oxidase to provide self-preservation.

50. A kit as recited in claim 48, wherein said composition further comprises water.

51. A kit as recited in claim 48, wherein said composition further comprises oxygen.

52. A kit as recited in claim 48, wherein said composition further comprises lactoperoxidase.

* * * * *